United States Patent [19]

Martens, III et al.

[11] 4,220,281

[45] Sep. 2, 1980

[54] VAPOR-DISPENSING DEVICE

[75] Inventors: Edward J. Martens, III; Phillip J. Neumiller, both of Racine County, Wis.

[73] Assignee: S. C. Johnson & Son, Inc., Racine, Wis.

[21] Appl. No.: 4,104

[22] Filed: Jan. 17, 1979

[51] Int. Cl.³ .............................................. A61L 9/04
[52] U.S. Cl. .................................... 239/57; 206/0.5; 239/59
[58] Field of Search .......................... 239/34, 53–60; 206/0.5; 229/9–11, 19, 20

[56] References Cited

U.S. PATENT DOCUMENTS

| | | | |
|---|---|---|---|
| 2,896,853 | 7/1959 | Curran | 239/60 X |
| 3,027,678 | 4/1962 | Whitney et al. | 206/0.5 X |
| 3,807,082 | 4/1974 | Hautmann et al. | 239/55 X |

FOREIGN PATENT DOCUMENTS 7308761 12/1974 Netherlands ............................... 239/59

Primary Examiner—Andres Kashnikow

[57] ABSTRACT

A dispenser for vapors characterized by an upstanding enclosure made of folded flexible sheet stock and having two upstanding opposed primary dispensing walls, one or more structural members within the enclosure to provide reinforcing dimensional stability between the primary walls and releasably holding a vaporizable composition, and air flow channels from one dispensing wall to the other. Preferred embodiments relate to variations in the structural member(s), the specific materials used, a barrier used to prevent loss of vaporizable composition by wicking and an impermeable film tightly wrapped therearound. The invention can be used for dispensing air fresheners, insecticides, and other air-treating vapors.

11 Claims, 8 Drawing Figures

U.S. Patent  Sep. 2, 1980  Sheet 1 of 2  4,220,281
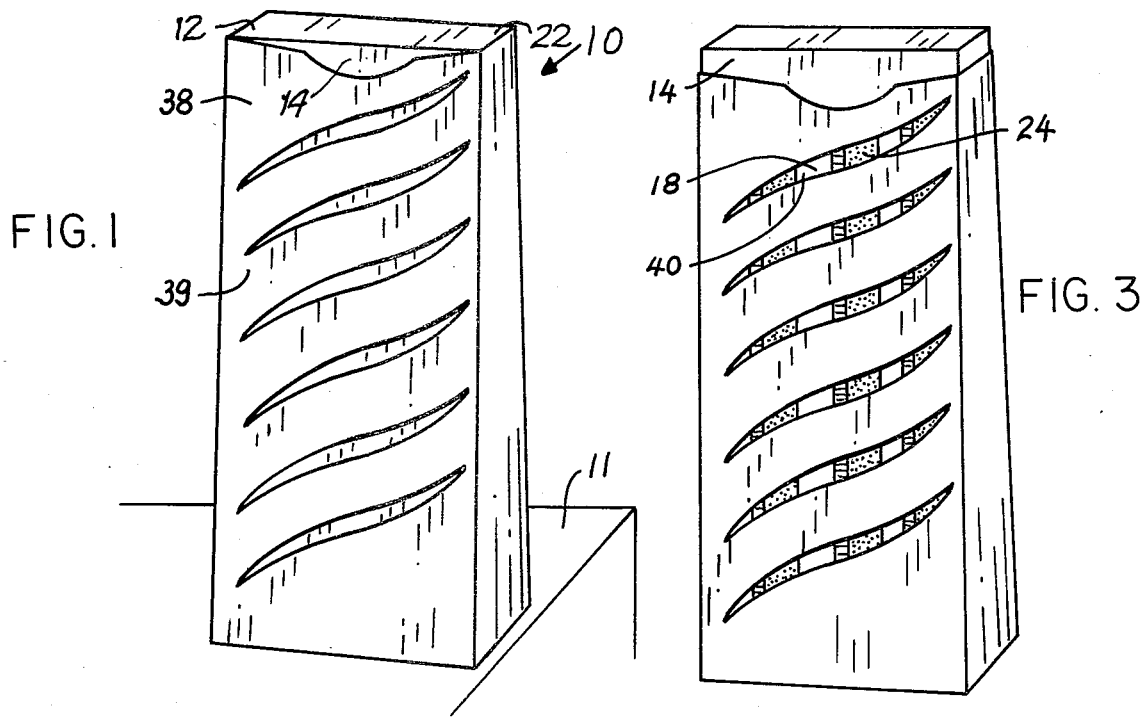
FIG. 1
FIG. 3
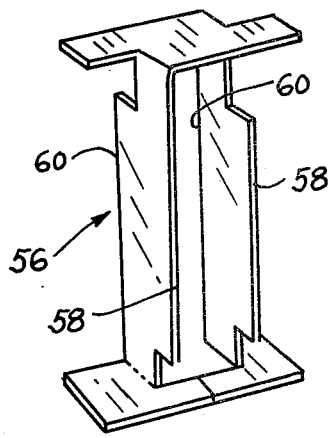
FIG. 6
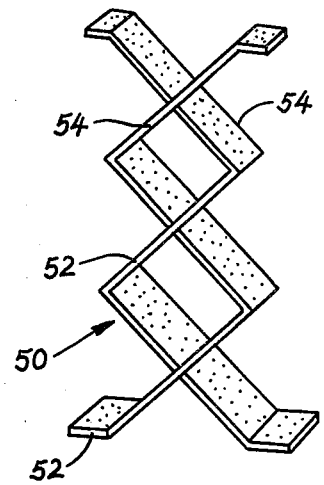
FIG. 5
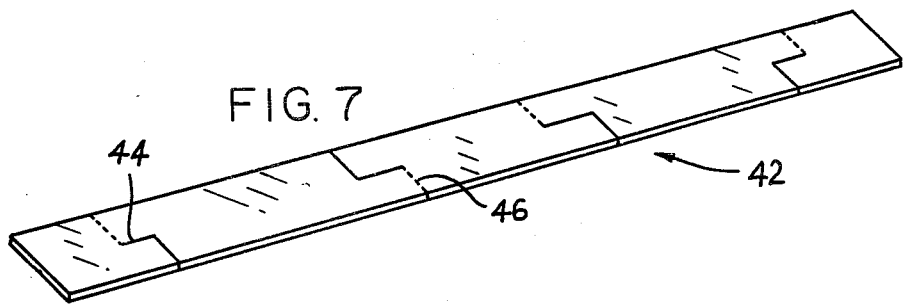
FIG. 7

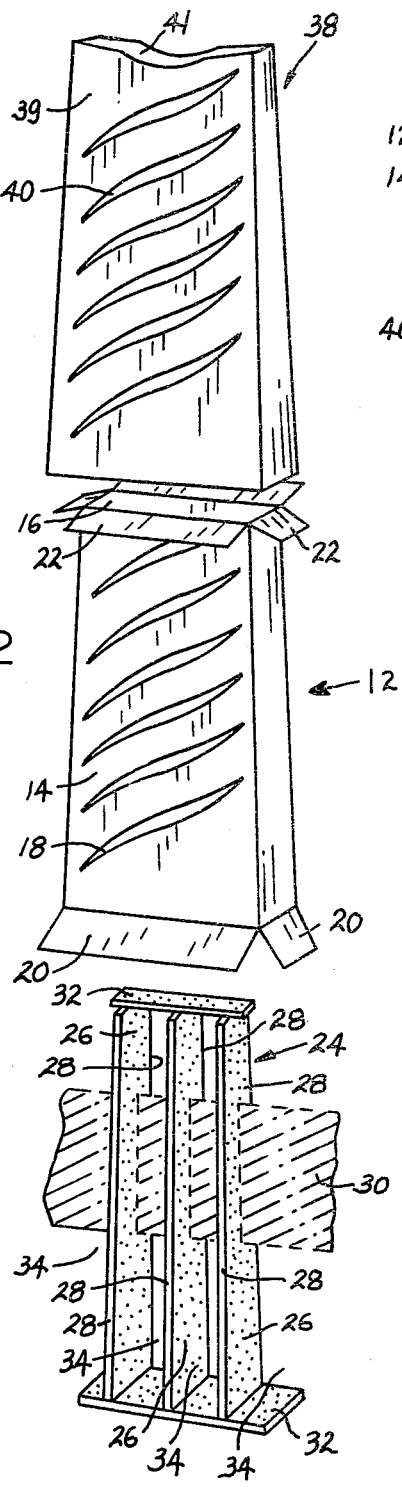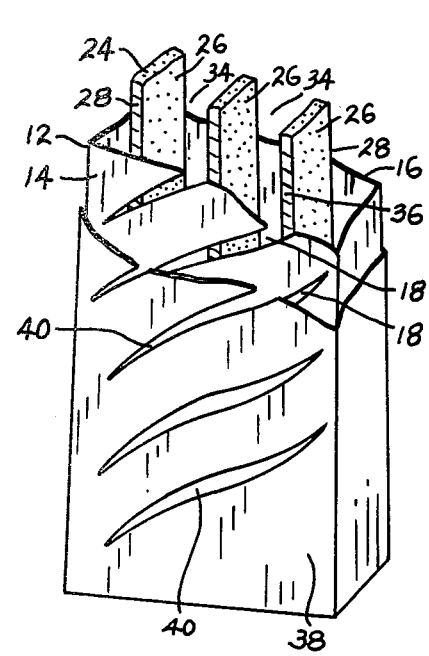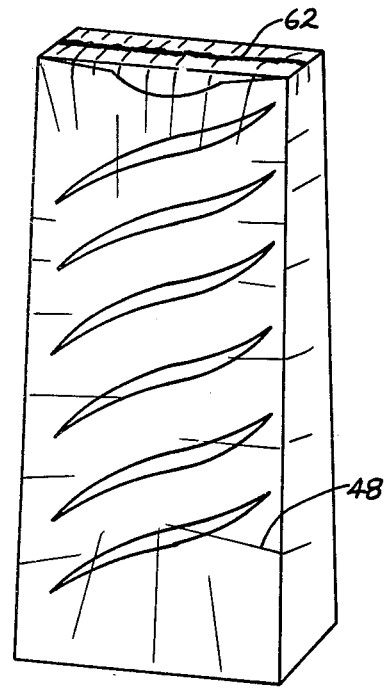

VAPOR-DISPENSING DEVICE

FIELD OF THE INVENTION

This invention relates generally to devices for dispensing vaporized compositions to the surrounding atmosphere. More particularly, the invention relates to devices which can provide both a continuous slow emission of air-treating vapors and a rapid emission of vapors for some specific purpose whenever desired. The invention relates to devices for imparting the refreshening effect of a vaporized deodorant to the atmosphere, or for dispensing insecticide vapors, insect repellent vapors, medicinal vapors, decongestant vapors or other vaporized compositions.

BACKGROUND OF THE INVENTION

The need for effectively combating airborne malodors in homes and enclosed public buildings, by odor masking or destruction, is well established. Various kinds of vapor-dispensing devices have been employed for this purpose. The most common of such devices is the aerosol container which propels minute droplets of an air freshener composition into the air. Another common type of dispensing device is a dish or mount of some kind containing or supporting a body of gelatinous matter (a "gel") which when it dries and shrinks releases a vaporized air-treating composition into the atmosphere. Other products such as deodorant blocks and liquid wicks are also used for dispensing air-treating vapors into the atmosphere by evaporation. Another group of vapor-dispensing devices utilizes a carrier material such as paperboard impregnated with (or in some cases coated by) a vaporizable composition. It is to the latter type of device that the invention is applicable. Such carrier materials, unlike the previously mentioned gels, do not undergo substantial shrinkage as the compositions vaporize.

Each of the above-mentioned devices have drawbacks as an approach to the entire problem of combating airborne malodors. The aerosol device dispenses mists or vapors in relatively large quantities over a short period of time to counteract intense and immediate malodors as are common in kitchens and bathrooms. A drawback of such devices, however, is that while they can counteract intense and immediate malodors they are not suited for lingering ambient odors which often exist in a closed space.

Many other types of products, such as gels, blocks, and liquid wicks, are generally suitable for the lingering malodors. These products normally require no attention, automatically dispensing their deodorants by evaporation. However, such dispensing is usually at a low rate which is often insufficient to counteract intense and immediate malodors.

Vapor-dispensing devices of the type utilizing a carrier material such as paperboard or the like may be advantageously designed for usefulness both against lingering low level malodors and intense and immediate malodors. In such products the carrier material has a predetermined form of its own and may be shaped, arranged, or suspended in a manner allowing circulation of ambient air with respect thereto. The carrier material is impregnated with (or coated by) a vaporizable composition. The vaporization may be increased or decreased depending on air movement and vapor concentration in the air adjacent the vaporizable composition. The normal slow emission of air-treating vapors from such devices may intentionally be increased by increasing air flow with respect to the impregnated materials, by waving the device in the air, by pumping, or the like. Examples of this type of vapor-dispensing product are the devices of U.S. Pat. No. 3,790,081, "Vapor Dispensing Device," to Thornton and Whyte, and U.S. Pat. No. De.250,041, "Air Fresheners," to George Schimanski. The instant invention is an improvement in this general type of vapor-dispensing device.

A major goal in the field of air freshener products, including those of the type last mentioned above, is development of functionally superior devices which can be inexpensively produced and thus disposed of without undue wastefulness when their vaporizing compositions are depleted. In some cases, the product developer has been forced to choose between the relative wastefulness involved in the discarding of a well-constructed, expensive air freshener device on the one hand, and the inconvenience involved in reusing a well-constructed, expensive air freshener device (for example, by reloading it with fresh impregnated carrier material after discarding the depleted material). A third alternative, which is totally unacceptable to some, is an inexpensive, substantially inferior, poorly-constructed device.

Certain specific products of the prior art are relatively expensive plastic constructions the discarding of which is, and is perceived to be, wasteful. Less expensive constructions, however, tend to be crushable, flimsy, and often irregular in dimension and in strength. And, particularly after rough handling during shipment, inexpensive constructions may not stand upright on a level surface with any degree of stability. Because of their weak construction, such devices can tend to be unstable.

BRIEF SUMMARY OF THE INVENTION

This invention provides a vapor-dispensing device of the type having a carrier material impregnated with or coated by a vaporizable, air-treating composition and allowing both slow emission of air-treating vapors and rapid emission when desired. The inventive vapor-dispensing device may be made of inexpensive materials, such as paperboard and the like, yet has substantial reinforcement, crush-resistance, and dimensional stability so as to provide an attractive device and a device readily adapted for stable placement on tabletops and other level surfaces.

In short summary, the invention is a dispenser of vapors having an upstanding enclosure formed of folded flexible sheet stock, such as relatively flexible lightweight, thin-gauge paperboard, and including two upstanding opposed primary walls (or "surfaces") which define dispensing openings to emit vapors from within the enclosure. The invention is further characterized by a carrier structure (sometimes referred to as the "structural means") disposed within the enclosure which serve(s) a number of functions: providing reinforcing dimensional stability between the primary dispensing walls of the enclosure; defining air flow channels through the enclosure from one of the primary walls to the other; and, at the same time, releasably holding a vaporizable composition, such as an air freshener liquid.

The dispensers of this invention are relatively inexpensive because of the construction which is used. The folded flexible sheet stock which is required for the upstanding enclosure is quite typically much less expensive than extruded, molded, or otherwise formed enclosure structures. In a highly preferred embodiment, the sheet stock is lightweight flexible paperboard and the structural means is relatively rigid, usually heavier and thicker paperboard which is impregnated with the vaporizable composition. Such constructions compare favorably in cost with certain other widely used air freshener devices. Yet, in spite of the inexpensive materials used, particularly the flexible foldable stock used in forming the enclosure, the inventive device provides a sturdy, crush-resistant, reinforced dispenser.

In one preferred embodiment, the carrier structure includes one or more pieces substantially perpendicular to a reference plane midway between the two primary walls and having edges which are in contact with the primary walls. By this structure, the opposed primary walls are maintained in a generally fixed, spaced relationship which can be maintained despite the application of pressure to the opposed primary walls. A preferred arrangement includes upstanding boards disposed in parallel planes.

Another preferred embodiment further requires that a barrier means which is impermeable to the vaporizable composition be disposed between the sheet stock and the impregnated structural means at contact points to prevent wicking of the composition from the carrier structure to the sheet stock. If undesirable wicking occurs, control of the dispensing of vapors over the life of the product is made more difficult. A barrier to maintain all unevaporated composition within the impregnated internal structure allows greater consistency in and control of vapor dispensing. Furthermore, a barrier eliminates unsightly discoloration or staining of the enclosure.

A highly preferred embodiment includes means to open and close the openings in the primary walls, to regulate the dispensing of vapors. This can be accomplished with a variety of devices. However, a shutter-like device in which openings move into alignment to open and out of alignment to close is most preferred.

As a means of restricting or preventing dispensing of vapors before dispensing is intended, the entire dispenser may be tightly wrapped in a substantially vapor-tight film wrapper. The so-called "shrink wraps" are particularly useful for this purpose. The reinforced character of the structure of this invention makes tight wrapping possible without crushing or causing deformation of the dispenser.

OBJECTS OF THE INVENTION

The primary object of this invention is to provide a superior and inexpensive vapor-dispensing device of the type allowing both slow emission of air-treating vapors and rapid emission when desired.

Another object of this invention is to provide a vapor-dispensing device constructed of inexpensive materials yet having substantial crush resistance, integrity of shape, and good dimensional stability.

Another object of this invention is to provide an inexpensive yet reliable vapor-dispensing device.

Still another object of this invention is to provide a disposable vapor-dispensing device which may be disposed of without wastefulness and without a significant perception of wastefulness.

Another object of this invention is to provide a vapor-dispensing device having superior operational characteristics while being inexpensive in construction.

BRIEF DESCRIPTION OF THE DRAWINGS

These and other important objects of the invention will become apparent from the following descriptions and from the drawings showing preferred embodiments wherein:

FIG. 1 is a perspective view of a preferred dispensing device of this invention.

FIG. 2 is an exploded perspective view of the device of FIG. 1.

FIG. 3 is another perspective view of the device of FIG. 1, showing it in open, dispensing condition.

FIG. 4 is a fragmentary, cut-away, perspective view of the device of FIG. 1, illustrating the relationship of the principal parts of the invention.

FIG. 5 is an alternate embodiment of the carrier structure used in this invention.

FIG. 6 is another alternate embodiment of the carrier structure used in this invention.

FIG. 7 illustrates the device of FIG. 6 in a non-erected condition.

FIG. 8 illustrates the device of FIG. 1 tightly covered by a vapor-tight film wrapper.

DESCRIPTION OF PREFERRED EMBODIMENTS

FIG. 1 shows a dispenser 10 according to this invention standing upright upon a level surface 11, such as a tabletop or the like. Dispenser 10 includes an upstanding (that is, usually vertically oriented) enclosure 12 which is formed of folded flexible sheet stock, such as lightweight paperboard or cardboard, and includes two upstanding opposed primary walls 14 and 16, each of which defines dispensing openings 18.

Enclosure 12 may be formed by steps such as cutting, scoring, folding, gluing, and the like, performed on flexible sheet stock. Enclosure 12 is completed by the closing of bottom flaps 20 and top flaps 22, shown in FIG. 2. The folded flexible sheet stock used in forming enclosure 12 may be various grades of preferably lightweight paperboard, foldable plastic sheet materials, plastic and foil laminates, paper and foil laminates, coated paper, and other flexible, foldable materials. Suitable paperboard materials include solid bleached sulphate paperboard, clay-coated news bark, kraft board, and the like. Suitable flexible, foldable paperboard preferably has a thickness within the range of 0.025-0.075 cm. Plastic materials usually may be of lesser thickness to achieve the same flexibility.

Inside enclosure 12 is a carrier structure 24 which serves at least three functions, that is, to reinforce enclosure 12, to provide the source of vaporizable composition within dispenser 10, and to define air flow channels through dispenser 10. Structure 24 may be made of substantially rigid paperboard which is impregnated with a vaporizable composition for dispensing as vapors during use. A great variety of other materials are usable for carrier structure 24, as will be mentioned hereafter. Structure 24 extends between opposed primary walls 14 and 16 of enclosure 12 in contact therewith to brace surfaces 14 and 16 apart in a manner providing dimensional stability therebetween.

As illustrated best in FIGS. 2, 3, and 4, reinforcing carrier structure 24 has upstanding parallel boards 26 which have edges 28 in contact with opposed primary walls 14 and 16 all along dispenser 10 from top to bottom. Furthermore, substantially parallel boards 26 are oriented substantially perpendicular to a reference plane 30 midway between primary walls 14 and 16. Such substantially perpendicular orientation is especially advantageous to the reinforcing function of carrier structure 24. In the embodiment shown, opposed primary walls 14 and 16 are themselves substantially planar and substantially parallel. Accordingly, parallel boards 26 of reinforcing structure 24 are substantially perpendicular to primary walls 14 and 16 as well as to reference plane 30.

Reinforcing carrier structure 24 is preferably made of substantially rigid paperboard such as J-5 cellulosic board (from Filter Materials, Inc., Waupaca, Wisconsin). Usable paperboard materials may have widely varying thicknesses to achieve the substantial rigidity required. Required thickness will be dependent on such things as porosity, binders used in the paperboard, density and many other factors. The J-5 material thickness is on the order of 0.3 cm., and given its density and other characteristics it has sufficient rigidity to reinforce an enclosure and provide dimensional stability between the opposed primary walls of an enclosure according to this invention. The paperboard materials and other materials usable in the carrier structure must have sufficient rigidity to perform the reinforcement function, that is, to provide crush resistance and dimensional stability for the upstanding enclosure.

Examples of other suitable materials for the carrier structures forming part of this invention are rigid felt, wood and rigid polyurethane foam. Crosslinked plastics containing the vaporizable composition such as HO fragrance polymer K series (from Hydro Optics, Inc., Valley Stream, New York), and thermoplastic rigid polymers capable of containing perfume or other vaporizable compositions such as VERSAMID 1635 (from General Mills, Minneapolis, Minnesota), are also acceptable. Other acceptable carrier structures, which may be coated with vaporizable compositions, may be dense, hard materials, since porosity is unnecessary. Suitable materials for the carrier structure will be apparent to those skilled in the art who have knowledge of this invention.

Parallel board 26 of reinforcing carrier structure 24 are secured at their top and bottom ends to mounting pieces 32, as shown in FIG. 2. Parallel boards 26 are glued to mounting pieces 32 to maintain parallel boards 26 in the proper side-to-side spacing. In manufacture, the sub-assembly formed by mounting pieces 32 and parallel boards 26 may be inserted into enclosure 12 before the closing of bottom flaps 20. After insertion, reinforcing carrier structure 24 provides strength and crush resistance to enclosure 12 and dimensional stability between opposed primary walls 14 and 16.

Reinforcing structure 24 defines air-flow channels 34 between primary walls 14 and 16, and allows the free passage of ambient air through openings 18 of primary walls 14 and 16 and through the entire dispenser 10. Such air passage facilitates the vaporization and dispensing of vapors, and constitutes an improvement over devices in which free air flow is much more restricted.

The carrier structure is somewhat isolated within the upstanding enclosure. Therefore, the vaporizable composition which it carries will be shielded to some extend from ambient air flow, retarding vaporization as the space within the enclosure adjacent to the carrier structure becomes somewhat saturated with vapors. This allows only low level vapor emission. However, if ambient air flow though the air flow channels is increased, such as by waving the device from side to side, the dispensing of vapors will be increased and the evaporation rate will accelerate as the air having a higher concentration of vapors is replaced by relatively fresh ambient air. By this means, good control of both lingering malodors and intense malodors can be achieved.

As illustrated in FIG. 4, a coating 36 is applied to the vertical edges of parallel boards 26. Coating 36, which is a barrier material impermeable to the vaporizable composition, is disposed between the sheet stock which forms enclosure 12 and reinforcing carrier structure 24 to prevent wicking of the vaporizable composition from the reinforcing carrier structure to the sheet stock. As an alternative to covering or coating the edges of reinforcing carrier structure 24, portions of the inner surface of enclosure 12 which are contacted by reinforcing carrier structure 24 may be coated with a barrier material which is impermeable to the vaporizable composition being used. A coating for enclosure 12 may be applied before enclosure 12 is erected by print-coating of the sheet stock. A barrier is unnecessary when the sheet stock used to form enclosure 12 is a material which does not absorb the vaporizable composition.

Suitable barrier materials must be substantially impermeable to the vaporizable composition in its liquid state. Examples of barrier materials are polyvinyl alcohol, polyvinyl acetate, polyethylene, polypropylene, acrylic polymers, various waxes and foils. Barrier materials can be applied by spraying, roller coating, gluing, taping, dipping, or other known methods. In some cases, a barrier may be a coating over the entire carrier structure, provided such coating is substantially impervious to the composition in its liquid form but allows diffusion of the composition in its evaporated form. Such a coating may serve the additional function of controlling the release of vapors, as will be mentioned later herein.

The embodiments shown in the drawings include a cover 38 which has major walls 39 and 451. Walls 39 and 41 each define openings 40 which are congruent to and arranged in the same pattern as openings 18 in primary walls 14 and 16. Openings 40 may be moved into registry with openings 18 by relative sliding movement between enclosure 12 and cover 38. The closed condition of dispenser 10, in which openings 40 and openings 18 are out of alignment, is illustrated in FIGS. 1 and 4. The open condition, in which openings 40 of cover 38 and openings 18 of enclosure 12 are aligned, is illustrated by FIG. 3. Such open condition is achieved by sliding enclosure 12 upwardly within cover 38.

FIGS. 5 and 6 illustrate alternate embodiments of a reinforcing carrier structure which can be placed within enclosure 12. Each of these alternate structures includes pieces which would be substantially perpendicular to a reference plane midway between the opposed primary walls of an enclosure such as enclosure 12. Such substantial perpendicularity provides good crush resistance, reinforcement, and dimensional stability to the enclosure, and also allows good air flow channels through the dispenser.

Carrier structure 50 of FIG. 5 is formed of two slotted, interlocked pieces. Its edges 52 and 54 would engage primary walls 14 and 16, respectively, of enclosure 12. Carrier structure 56 of FIG. 6 has edges 68 and 60 which would engage primary walls 14 and 16, respectively. FIG. 7 illustrates a relatively rigid paperboard blank 42 having cuts 44 (illustrated by solid lines) and scores or creases 46 (illustrated by dotted lines) which allow reinforcing carrier structure 56 to be made without separate mounting pieces. Paperboard blank 42 may be erected into the condition illustrated in FIG. 6 and then inserted through an end of enclosure 12 before enclosure 12 is closed. Carrier structure 50, like structure 56, requires no additional mounting pieces.

A great variety of other shapes and arrangements of materials may be used to form the structural means disposed within enclosure 12. Convoluted rolls of corregated cardboard, honeycomb configurations, criss-cross configurations and V-shaped configurations are a few examples. The structure must, however, serve the multiple purposes of providing reinforcing dimensional stability between the opposed primary walls of an enclosure formed of flexible folded sheet stock, defining air flow channels through the dispenser, and releasably carrying the vaporizable composition.

The number of vaporizable compositions which can be used for various applications is almost limitless. In the field of air fresheners, it is preferred to use perfumes or perfumes dissolved in a volatile, odorless solvent. The isoparaffinic hydrocarbon solvents, such as those sold under the trademark ISOPAR (by Exxon Company, U.S.A.), are preferred as solvents for this purpose.

In the field of medicinal uses, camphor may be dissolved in a solvent such as an isoparaffinic hydrocarbon. Menthol eucalyptus may be used in the same manner as camphor. Thymol may also be used in the same way or may be used in combination with camphor or menthol eucalyptus or both in a suitable solvent.

For insecticides, preferred vaporizable compositions are pyrethrins and dimethyl dichlorovinyl phosphate and its related compositions. Insect repellants which may be dispensed with the device of our invention are exemplified by 2-ethyl hexanediol; N, N-diethyl toluamide; and citronella.

The vaporizable composition may include various modifiers to control the vaporization. For example, various components may be included to retard evaporation of perfumes, for example, and thus retard the release of vapors from the device. Surfactants such as ethoxylated alkyl phenols like SURFONIC N-10 (from Jefferson Chemical, Houston, Texas) are useful for this purpose. Other components which tend to decelerate vapor release include ethylene oxide/propylene oxide block copolymers such as PLURONIC L101 (from BASF Wyandotte, Wyandotte, Michigan), and fatty acid esters such as VARONIC EGS (from Ashland Chemical Company, Dublin, Ohio). Generally, retardation can be achieved by the addition of components which are less volatile than the perfume or other principal component of the vaporizable composition.

Release of vapors can generally be accelerated by addition of components which are more volatile than the principal component (e.g. perfume) of the vaporizable composition. The isoparaffinic hydrocarbon solvents, mentioned above, and alcohols may sometimes be used for this purpose.

Release of vapors can also be controlled by coating the carrier structure with a polymeric film through which the vaporizable composition can be diffused. Examples of films suitable for controlling the release of many perfumes are polyethylene, polypropylene, and plasticized polyvinyl chloride. The thickness of the covering film is another factor contributing to control.

Vapor release may also be controlled by partially coating the carrier structure with materials through which the vaporizable composition cannot pass. In other words, control is possible by increasing or decreasing the carrier structure surface area which is exposed to air. Release can also be controlled by increasing or decreasing the air flow through the device.

Reinforcing carrier structure 24 may be sprayed with the vaporizable composition or may be dipped into the vaporizable composition. A great number of other impregnating techniques may be used. It should also be pointed out that the vaporizable composition need not be impregnated into a porous reinforcing carrier structure, but can be a vaporizable coating on the carrier structure, which may be either porous or nonporous. Thus, reinforcing carrier structure 24 must releasably carry the vaporizable composition in some manner, the precise manner not being of great importance.

As illustrated in FIG. 8, a dispenser 10 may advantageously be surrounded, tightly wrapped and sealed by a substantially vapor-tight film wrapper 48. Such a film wrapper can prevent early, unintended loss of vapors. A tight film wrapping of dispenser 10 is made possible because of the reinforced nature of the inventive dispenser. A unreinforced structure would tend to be deformed or crushed by tight wrapping with a vapor-tight film. Suitable films include polyvinyl chloride, polyethylene, polypropylene, polyvinyl alcohol, polyvinyl acetate, nylon, polyvinylidene chloride, a polyester materials, and laminates of two or more materials. The choice of a film is dependent upon the vaporizable composition in the dispenser; a film should be chosen which is impermeable to the composition, preferably in both its liquid and vapor states.

A highly preferred type of film wrapper for use with this invention is a "shrink wrap" of the type which is applied loosely in sleeve form about an object to be wrapped, in some cases heat sealed at either end (see seal 62 in FIG. 8), and then passed with the object through a heated shrink tunnel or otherwise exposed to heat to cause the film to shrink and tightly engage the enclosed object. Suitable shrink wrap materials are known to those skilled in the art. A polyvinyl chloride shrink film, such as the film sold under the trademark SKINTIGHT NSM 60 by Gilbreth International Corporation of Cornwells Heights, Pennsylvania, is quite satisfactory. Various other shrink wrap materials would be quite acceptable.

Primary walls 14 and 16 of enclosure 12 and the adjacent covering walls 39 and 41 of cover 38 are substantially planar. However, the opposed, upstanding primary walls could be in other shapes. For example, walls 14 and 16 (and the adjacent covering walls of cover 38) could be bowed outwardly. Such a configuration would improve the sealing achieved by wrapper 48, which would then form a seal about each opening in the walls.

Enclosure 12 is shown with four upstanding walls. Other configurations are possible. For example, using bowed primary walls as just mentioned could allow an enclosure having only two upstanding walls.

While in the foregoing specification, this invention has been described in relation to certain preferred embodiments thereof and many details have been set forth for purpose of illustration, it will be apparent to those skilled in the art that the invention is susceptible to additional embodiments and that certain of the details described herein can be varied considerably without departing from the basic principles of the invention.

What is claimed is:

1. A dispenser of vapors comprising:

an upstanding enclosure formed of folded flexible sheet stock and including two upstanding opposed primary walls each defining dispensing openings; and structural means enclosed within the enclosure to provide reinforcing dimensional stability between the primary walls, the structural means defining air flow channels from one of the primary walls to the other, releasably holding a vaporizable composition, and maintaining said dimensional stability before, during, and after vaporization of said composition.

2. The dispenser of claim 1 wherein the structural means comprises at least one piece substantially perpendicular to a reference plane midway between the primary walls and having edges in contact with the primary walls.

3. The dispenser of claim 2 wherein said at least one piece comprises upstanding boards disposed in parallel planes.

4. The dispenser of claim 1 wherein the sheet stock is flexible paperboard and the structural means is substantially rigid paperboard impregnated with the vaporizable composition.

5. The dispenser of claim 4 further comprising barrier means impermeable to the composition disposed between the sheet stock and the structural means at contact points to prevent wicking of the composition from the structural means to the sheet stock.

6. The dispenser of claim 1 further comprising means to open and close the openings in the primary walls.

7. The dispenser of claim 2 wherein the sheet stock is flexible paperboard and the structural means is substantially rigid paperboard impregnated with the vaporizable composition.

8. The dispenser of claim 7 wherein said at least one piece comprises upstanding boards disposed in parallel planes.

9. The dispenser of claim 8 further comprising barrier means impermeable to the composition disposed between the sheet stock and the structural means at contact points to prevent wicking of the composition from the structural means to the sheet stock.

10. The dispenser of claim 8 further comprising means to open and close the openings in the primary walls.

11. The dispenser of claim 7 further comprising a substantially vapor-tight film outer wrapper tightly wrapped thereabout.

* * * * *